United States Patent
Ohse et al.

(10) Patent No.: US 11,700,998 B2
(45) Date of Patent: Jul. 18, 2023

(54) IMAGING MODULE

(71) Applicant: Fujikura Ltd., Tokyo (JP)

(72) Inventors: Koji Ohse, Sakura (JP); Wataru Oishi, Sakura (JP); Yoshinobu Numasawa, Sakura (JP)

(73) Assignee: Fujikura Ltd., Tokyo (JP)

( * ) Notice: Subject to any disclaimer, the term of this patent is extended or adjusted under 35 U.S.C. 154(b) by 57 days.

(21) Appl. No.: 17/339,090

(22) Filed: Jun. 4, 2021

(65) Prior Publication Data

US 2021/0393110 A1  Dec. 23, 2021

(30) Foreign Application Priority Data

Jun. 23, 2020 (JP) ................................ 2020-107466

(51) Int. Cl.
*A61B 1/05* (2006.01)
*A61B 1/00* (2006.01)
*A61B 1/06* (2006.01)

(52) U.S. Cl.
CPC .......... *A61B 1/051* (2013.01); *A61B 1/00009* (2013.01); *A61B 1/00018* (2013.01); *A61B 1/00059* (2013.01); *A61B 1/0661* (2013.01)

(58) Field of Classification Search
CPC .. A61B 1/00018; A61B 1/00059; A61B 1/051
See application file for complete search history.

(56) References Cited

U.S. PATENT DOCUMENTS

| 6,567,115 B1* | 5/2003 | Miyashita | A61B 1/051 348/76 |
| 2009/0198106 A1* | 8/2009 | Ichihashi | A61B 1/0684 600/178 |
| 2011/0249106 A1* | 10/2011 | Makino | H05K 1/189 29/829 |
| 2015/0190039 A1* | 7/2015 | Takahashi | A61B 1/05 600/109 |
| 2019/0069767 A1* | 3/2019 | Mikami | A61B 1/00114 |

FOREIGN PATENT DOCUMENTS

JP  H05-220107 A  8/1993

* cited by examiner

*Primary Examiner* — Aaron B Fairchild
(74) *Attorney, Agent, or Firm* — Osha Bergman Watanabe & Burton LLP

(57) ABSTRACT

An imaging module includes an imaging element including a light receiving surface, an electrode surface on a side opposite to the light receiving surface, and imaging element electrodes formed on the electrode surface, a substrate including a first surface, a second surface on a side opposite to the first surface, and a first end surface facing the electrode surface, a cable portion having a conductor electrically connected to the imaging element electrodes via a wire on the substrate, a sealing resin that covers at least the first surface and the second surface, and an identification resin attached to a portion of the sealing resin on the first surface or a portion of the sealing resin on the second surface.

8 Claims, 5 Drawing Sheets

IMAGING MODULE

CROSS-REFERENCE TO RELATED APPLICATIONS

Priority is claimed from Japanese Patent Application No. 2020-107466 filed on Jun. 23, 2020, the content of which is incorporated herein by reference.

TECHNICAL FIELD

The present invention relates to an imaging module.

BACKGROUND

Japanese Unexamined Patent Application, First Publication No. H5-220107 discloses an endoscope including a case (distal cover) and an imaging module having an imaging element attached in the case. The imaging element is connected to an image processing device or the like via the cable, and transmits image data. In such an endoscope, it is required to align top and bottom of an imaging element with respect to top and bottom of the case in order to align top and bottom of an image. Here, in recent years, a size of the imaging element has been reduced, and thus it may be difficult to distinguish the top and bottom of the imaging element by visually observing a shape of the imaging element.

SUMMARY

One or more embodiments of the invention provide an imaging module capable of easily distinguishing the top and bottom of an imaging element.

In one or more embodiments of the invention, there is provided an imaging module including: an imaging element including a light receiving surface, an electrode surface located on a side opposite to the light receiving surface, and a plurality of imaging element electrodes formed on the electrode surface; a substrate including a first surface, a second surface located on a side opposite to the first surface, and a first end surface facing the electrode surface; a cable portion having a conductor electrically connected to the imaging element electrodes via a wire on the substrate; a sealing resin that covers at least the first surface and the second surface; and an identification resin attached to a portion of the sealing resin located on the first surface or a portion of the sealing resin located on the second surface.

According to one or more embodiments, it is possible to easily recognize top and bottom of the imaging element by visually observing the identification resin. Therefore, it is possible to improve manufacturing efficiency of an endoscope and prevent the imaging element from being attached in the endoscope in a wrong direction.

Here, the identification resin may be an ultraviolet curable resin.

Further, an area of the identification resin when viewed from a thickness direction of the substrate may be 1.7 mm$^2$ or less.

Further, the cable portion may include a coaxial cable.

According to one or more embodiments of the invention, it is possible to provide the imaging module capable of easily distinguishing the top and bottom of the imaging element.

DETAILED DESCRIPTION

Hereinafter, an imaging module and an endoscope according to one or more embodiments will be described with reference to the drawings.

Figure 1:
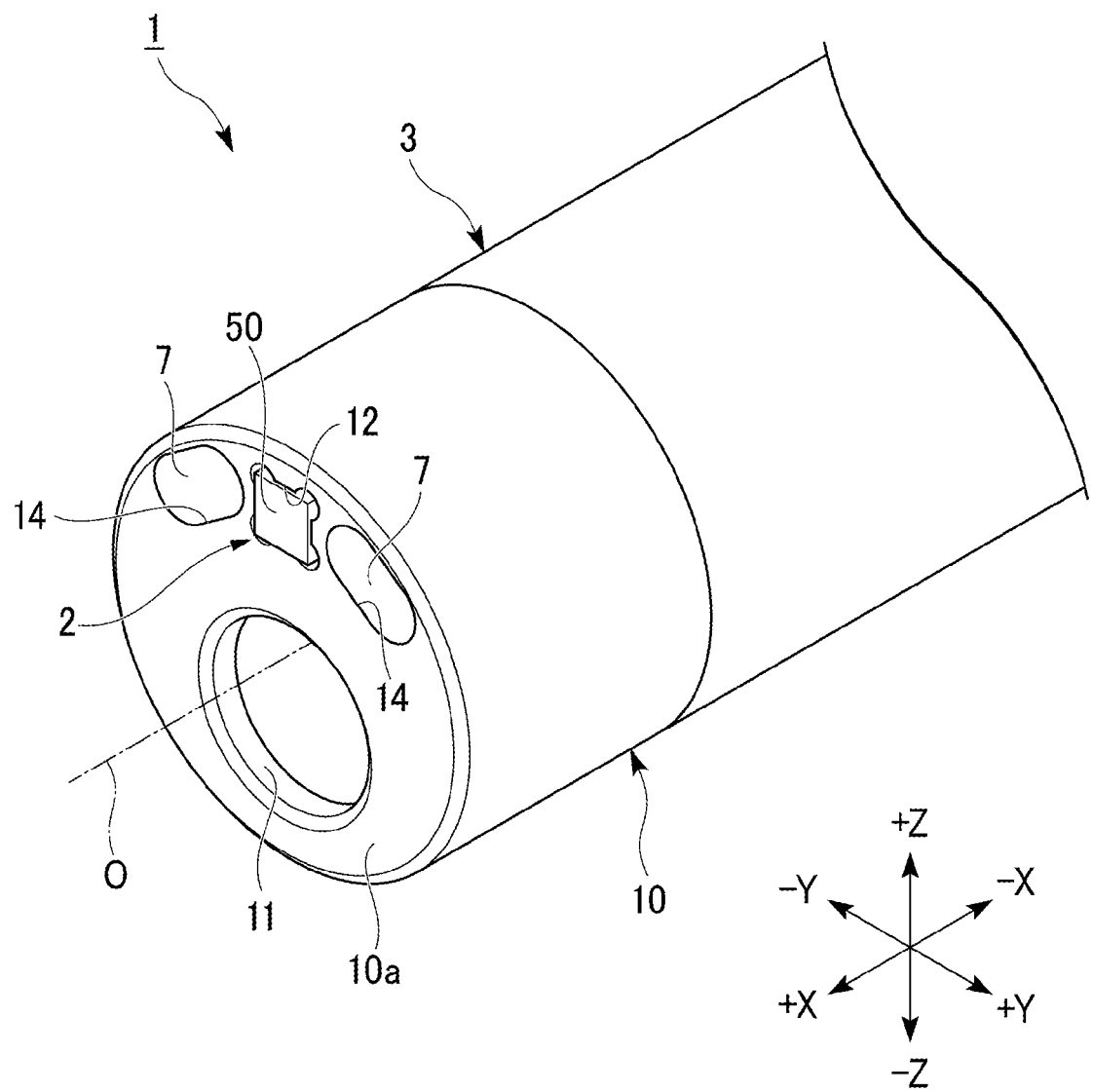
FIG. 1 is a perspective view of an endoscope according to one or more embodiments.
Figure 2:
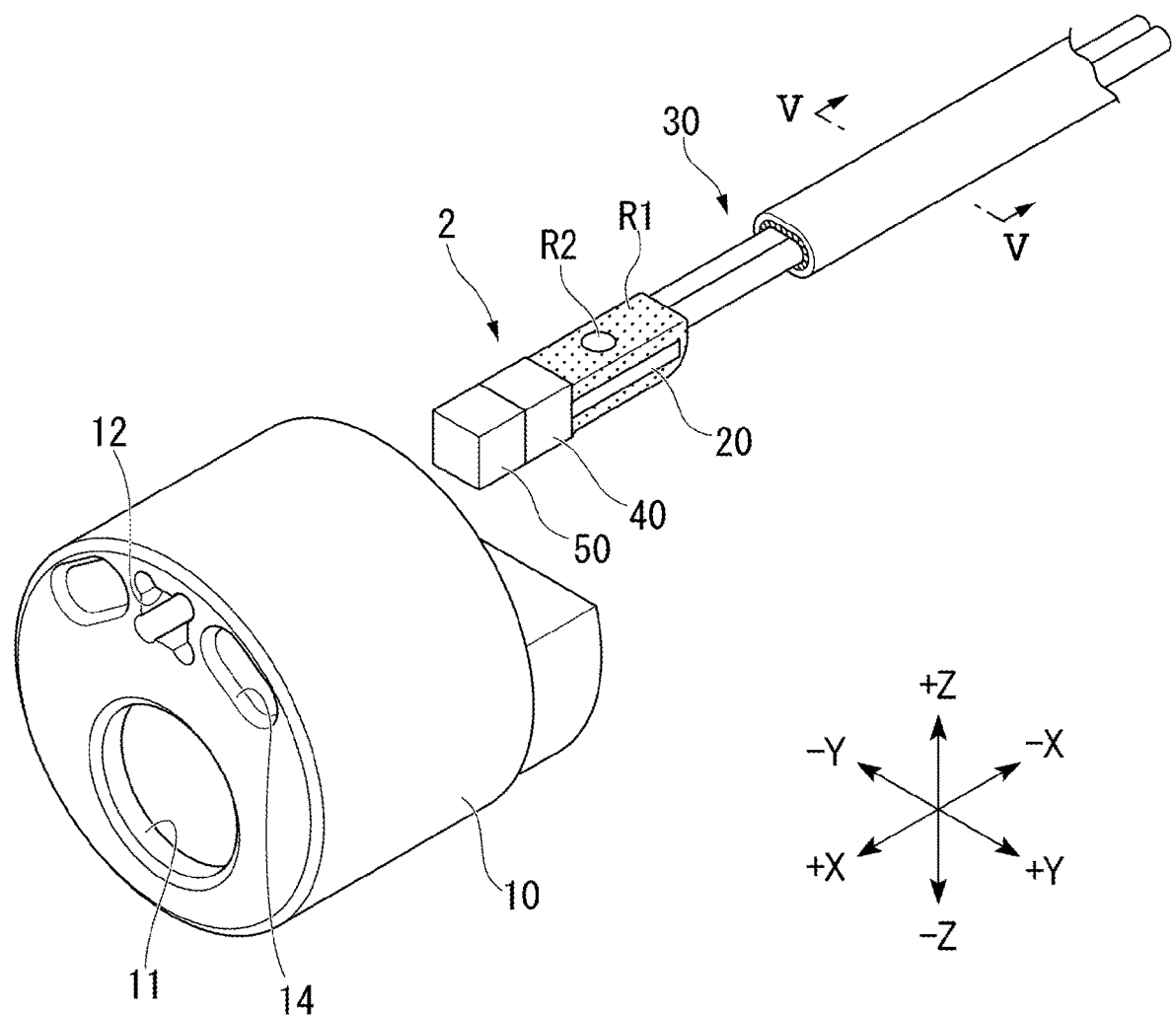
FIG. 2 is an exploded perspective view of the endoscope of FIG. 1.

As illustrated in FIG. 1, an endoscope 1 includes an imaging module 2, a sheath 3, and a case 10. As illustrated in FIG. 2, the imaging module 2 includes a substrate 20, a cable portion 30, an imaging element 40, and a lens unit 50.

(Direction Definition)

In one or more of the embodiments, an XYZ Cartesian coordinate system is set and a positional relationship of each configuration is described. A longitudinal direction of the endoscope 1 is represented by an X axis. In the longitudinal direction, a side closer to the lens unit 50 viewed from the cable portion 30 is referred to as a +X side or a front side, and the opposite side is referred to as a −X side or a rear side. A thickness direction of the substrate 20 is referred to as an up-down direction and is represented by a Z axis. The up-down direction is orthogonal to the longitudinal direction. One side (+Z side) in the up-down direction is referred to as an upper side, and the other side (−Z side) is referred to as a lower side. A direction orthogonal to both the longitudinal direction and the up-down direction is referred to as a right-left direction and is represented by a Y axis. One side (+Y side) on the Y axis is referred to as a right side, and the other side (−Y side) is referred to as a left side.

The case 10 is disposed at a front end portion of the endoscope 1. A portion (at least the lens unit 50) of the imaging module 2 is accommodated in the case 10. The case 10 has a channel 11, a camera accommodating portion 12, and two light projecting holes 14. The channel 11, the camera accommodating portion 12, and the light projecting holes 14 are open to a front end surface 10a of the case 10. The channel 11 and the camera accommodating portion 12 are disposed side by side in the up-down direction. The two light projecting holes 14 are disposed so as to interpose the camera accommodating portion 12 therebetween in the right-left direction.

By accommodating a treatment tool in the channel 11, the endoscope 1 can be used as a catheter. For example, the treatment tool includes various forceps, snares, guide wires, stents, laser treatment tools, high-frequency treatment tools, or the like. The lens unit 50 of the imaging module 2 is accommodated in the camera accommodating portion 12. An inside of each light projecting hole 14 is filled with a transparent resin 7. A light source (for example, an LED) is disposed behind the transparent resin 7, and light is launched to the front of the case 10 through the transparent resin 7. In FIG. 2, the transparent resin 7 or the like is omitted.

The imaging element 40 is an element capable of detecting light and generating an electric signal (image data) representing an image. As such an element, a solid-state imaging element (CMOS, CCD, or the like) including a semiconductor element in a light receiving portion is because of a small size thereof. Other examples of the imaging element 40 include an organic imaging element including an organic optical material in a light receiving portion, an imaging tube including an electron tube in a light receiving portion, or the like.

The lens unit 50 includes a tubular lens housing and a lens housed inside the lens housing. The lens unit 50 is fixed to a front end surface of the imaging element 40 so that an optical axis of the lens in the lens housing and a light receiving optical axis of the imaging element 40 coincide with each other. The imaging element 40 receives light that has passed through the lens unit 50 and takes an image.

Figure 3:
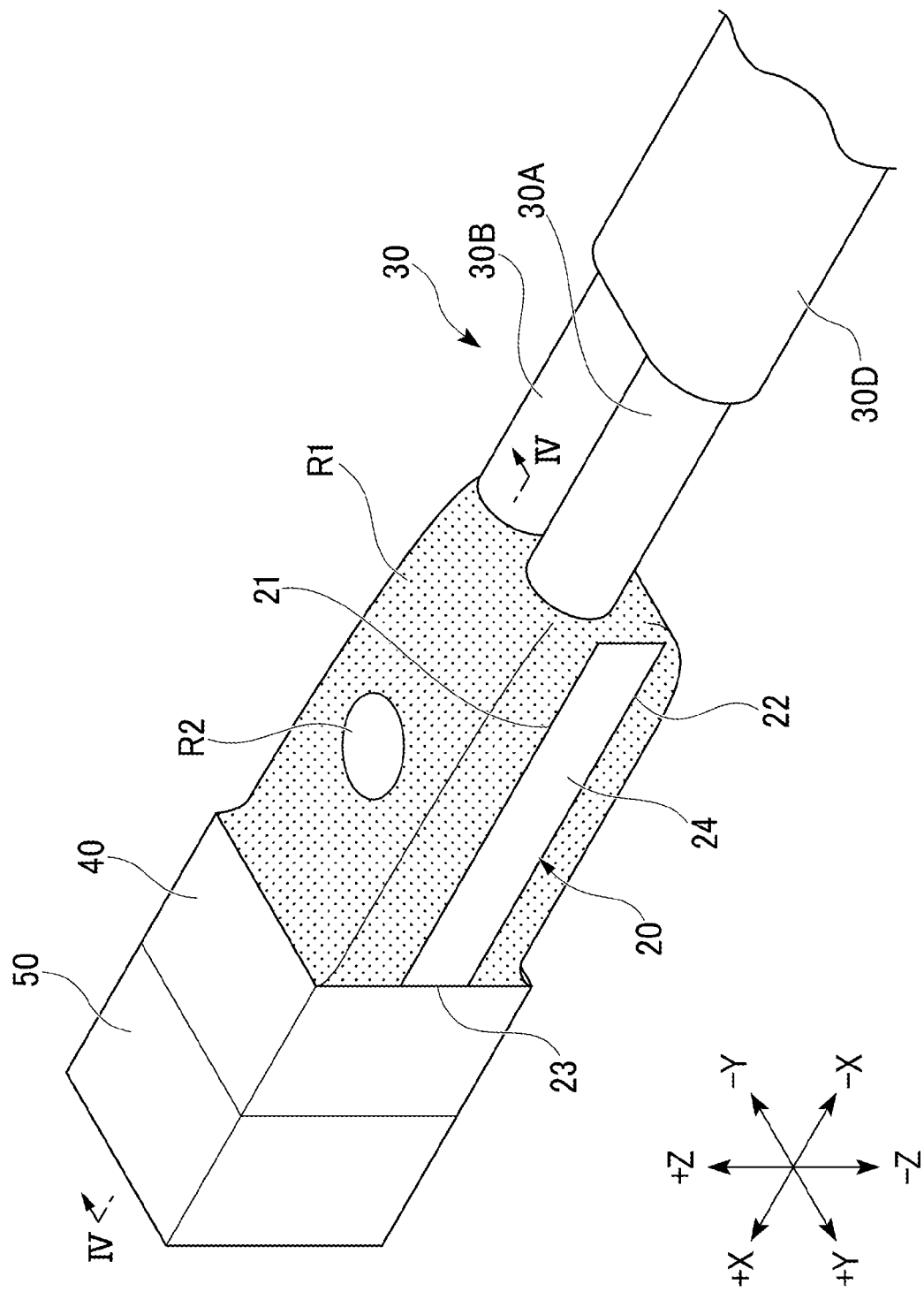
FIG. 3 is an enlarged view of an imaging module of FIG. 2.
Figure 4:
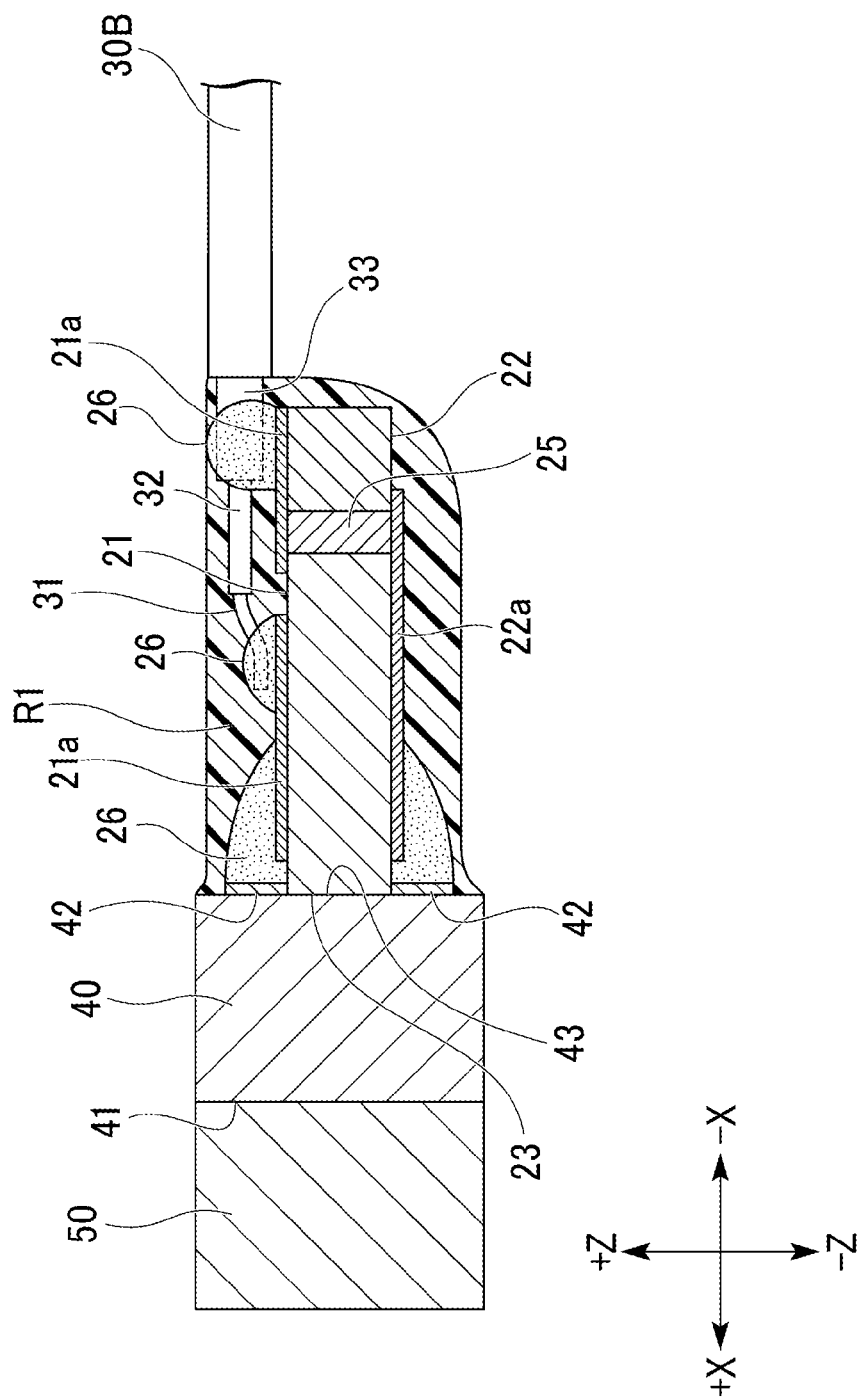
FIG. 4 is a cross-sectional view taken along line IV-IV of FIG. 3.

As illustrated in FIG. 3, the substrate 20 includes a first surface 21 facing upward, a second surface 22 facing downward, a first end surface 23 facing the front side, and a pair of side surfaces 24 facing the right-left direction. As illustrated in FIG. 4, wires 21*a* and 22*a* are formed on the first surface 21 and the second surface 22, respectively. A portion of the wire 21*a* (upper wire) formed on the first surface 21 and the wire 22*a* (lower wire) formed on the second surface 22 are electrically connected to each other by a through wire 25 passing through the substrate 20. The imaging element 40 is fixed to the first end surface 23. The through wire 25 is not essential, and a wire may be formed only on one of the first surface 21 and the second surface 22.

As illustrated in FIG. 4, the imaging element 40 includes a light receiving surface 41, an electrode surface 43 located on a side opposite to the light receiving surface 41, and a plurality of imaging element electrodes 42 provided on the electrode surface 43. The light receiving surface 41 faces the front side and receives light that has passed through the lens unit 50. The electrode surface 43 faces the rear side and faces the first end surface 23 of the substrate 20 in a front-rear direction. The imaging element electrodes 42 are disposed on the electrode surface 43. On the electrode surface 43, the imaging element electrodes 42 are disposed above the substrate 20, and below the substrate 20, respectively. The plurality of imaging element electrodes 42 and the wires 21*a* and 22*a* are electrically connected by a solder 26, respectively.

Figure 5:
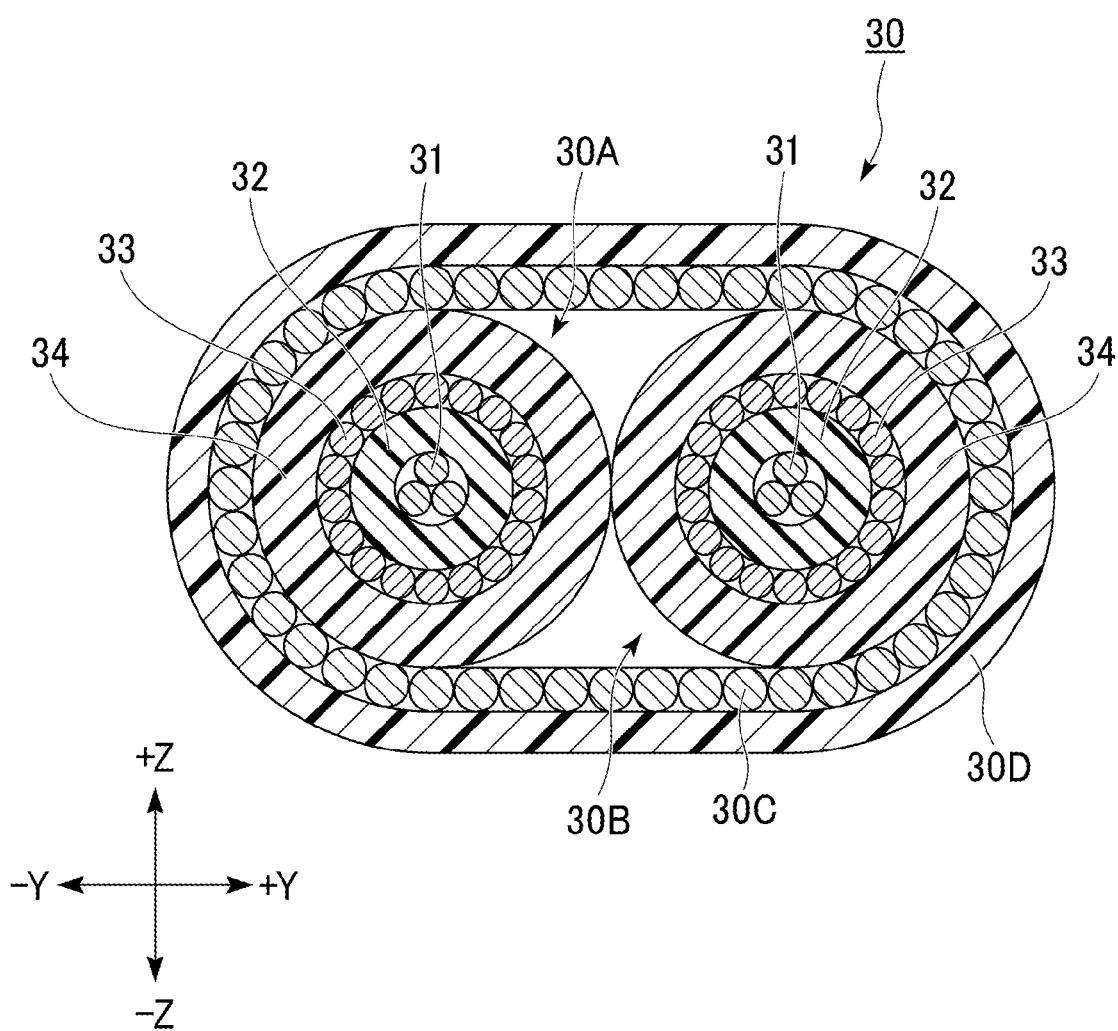
FIG. 5 is a cross-sectional view taken along line V-V of FIG. 2.

The cable portion 30 extends from the substrate 20 to the rear side. A rear end of the cable portion 30 is connected to an image processing device or the like. As illustrated in FIG. 5, the cable portion 30 includes a first coaxial cable 30A, a second coaxial cable 30B, a shield conductor 30C, and a cable jacket 30D. The first coaxial cable 30A and the second coaxial cable 30B are disposed side by side in the right-left direction. The shield conductor 30C is disposed so as to surround the two coaxial cables 30A and 30B. The cable jacket 30D accommodates the two coaxial cables 30A and 30B and the shield conductor 30C.

Structures of the first coaxial cable 30A and the second coaxial cable 30B are the same as each other. Specifically, each of the coaxial cables 30A and 30B has a central conductor 31, an internal insulator 32, an external conductor 33, and an external insulator 34. The central conductor 31 is located at a center of each of the coaxial cables 30A and 30B. The internal insulator 32 has a tubular shape and surrounds the central conductor 31. The external conductor 33 is disposed so as to surround the internal insulator 32. The external insulator 34 has a tubular shape and surrounds the external conductor 33.

As illustrated in FIG. 4, the central conductor 31 is electrically connected to the imaging element electrode 42 located above the substrate 20 via the wire 21*a*. The external conductor 33 is electrically connected to the imaging element electrode 42 located below the substrate 20 via the wire 21*a*, the through wire 25, and the wire 22*a*. For example, the central conductor 31 is used for transmitting a signal from the imaging element 40 to the image processing device or the like, or for transmitting a signal from the image processing device or the like to the imaging element 40. For example, the external conductor 33 is used to supply electric power to the imaging element 40. Configurations of the coaxial cables 30A and 30B are not limited to the above, and can be appropriately changed.

As illustrated in FIG. 3, a sealing resin R1 is provided on the substrate 20. The sealing resin R1 is used for sealing a wire on the substrate 20, and connection portions (solder portions) between the central conductor 31 and the wire on the substrate 20, and between the external conductor 33 and the wire on the substrate 20, or the like. As the sealing resin R1, any material that has insulating properties and can be cured after being applied on the substrate 20 in a state of having fluidity can be adopted. For example, the sealing resin R1 may be an ultraviolet curable resin or a thermosetting resin. Specific examples of the thermosetting resin include an epoxy resin. The sealing resin R1 covers the first surface 21 and the second surface 22 of the substrate 20. The sealing resin R1 may cover the side surface 24 of the substrate 20.

In one or more embodiments, the case 10 has an asymmetrical shape in the up-down direction. If an up-down orientation of the imaging element 40 is not matched with an up-down orientation of the case 10, an up-down orientation of the image data acquired by the imaging element 40 is inconsistent. A size of the case 10 is such that the up-down orientation can be recognized by visually observing a shape thereof. Further, it is also possible to provide a mark or the like indicating the top and bottom on an outer surface of the case 10. Meanwhile, a size of the imaging module 2 is very small, and even when dimensions of the lens unit 50, the imaging element 40, and the substrate 20 in the longitudinal direction are combined, for example, the dimensions may be about 2 mm. In such an extremely small imaging module 2, it may be difficult to recognize the up-down orientation of the imaging element 40 by visually observing the shape.

Therefore, in one or more embodiments, an identification resin R2 is attached to a portion of the sealing resin R1 located on the first surface 21. Therefore, an operator who assembles the endoscope 1 can easily recognize that a side to which the identification resin R2 is attached is the upper side (first surface 21 side) by visually observing the identification resin R2. As the identification resin R2, any material can be used as long as it can be distinguished from the sealing resin R1. For example, one of the sealing resin R1 and the identification resin R2 may be white and the other may be black. Further, considering easiness of work when curing the identification resin R2 after applying the liquid identification resin R2 to the sealing resin R1, the identification resin R2 is an ultraviolet curable resin.

In one or more embodiments, the identification resin R2 has a substantially circular shape when viewed from the up-down direction (thickness direction of the substrate 20). However, the shape of the identification resin R2 is not limited to a circular shape, and may be a non-circular shape such as an elliptical shape. As examined by the inventors of the present application, an area of the identification resin R2 when viewed from the up-down direction is 0.03 mm$^2$ or more and 1.7 mm$^2$ or less. By setting the area of the identification resin R2 to 0.03 mm$^2$ or more, the identification resin R2 can be visually recognized more reliably. Further, by setting the area of the identification resin R2 to 1.7 mm$^2$ or less, for example, it is possible to prevent the identification resin R2 before curing applied to the portion of the sealing resin R1 located on the first surface 21 from wrapping around the side surface 24 of the substrate 20 or the like downward.

In FIG. 2 or the like, the identification resin R2 is attached to the sealing resin R1 above the substrate 20, but the identification resin R2 may be attached to the sealing resin R1 below (second surface 22 side of) the substrate 20. In this case, the operator assembling the endoscope 1 can easily recognize that a side to which the identification resin R2 is attached is the lower side by visually observing the identification resin R2.

As described above, in one or more embodiments, the imaging module 2 includes the imaging element 40 including the light receiving surface 41, the electrode surface 43 located on the side opposite to the light receiving surface 41, and the plurality of imaging element electrodes 42 formed on the electrode surface 43, the substrate 20 including the first surface 21, the second surface 22 located on the side opposite to the first surface 21, and the first end surface 23 facing the electrode surface 43, the cable portion 30 having the conductor (central conductor 31 or external conductor 33) electrically connected to the imaging element electrodes 42 via the wires 21a and 22a on the substrate 20, the sealing resin R1 that at least covers the first surface 21 and the second surface 22, and the identification resin R2 attached to a portion of the sealing resin R1 located on the first surface 21 or a portion of the sealing resin R1 located on the second surface 22. According to the configuration, it is possible to easily recognize the top and bottom of the imaging element 40 by visually observing the identification resin R2. Therefore, it is possible to improve manufacturing efficiency of the endoscope 1 and prevent the imaging element 40 from being attached to the case 10 in a wrong direction.

Further, the identification resin R2 may be an ultraviolet curable resin. In this case, after the identification resin R2 is applied to the sealing resin R1, a work of curing the identification resin R2 becomes easy. Therefore, it is possible to further improve the manufacturing efficiency of the endoscope 1.

Further, the area of the identification resin R2 when viewed from the thickness direction of the substrate 20 may be 1.7 mm² or less. The area of the identification resin R2 when viewed from the thickness direction of the substrate 20 may be in the range of 0.1 mm² or more and 0.5 mm² or less. In this case, while making the identification resin R2 more reliable and visible, it is possible to further prevent the identification resin R2 before curing from attaching to an unintended portion of the sealing resin R1.

Further, the cable portion 30 may include the coaxial cables 30A and 30B.

A technical scope of the present invention is not limited to the above-described embodiments, and various modifications can be made without departing from a spirit of the present invention.

For example, the cable portion 30 of the above embodiments includes two coaxial cables 30A and 30B, but the number of coaxial cables can be changed as appropriate. That is, the cable portion 30 may have only one coaxial cable or three or more coaxial cables. Alternatively, the cable portion 30 does not have to include the coaxial cable.

Further, an electronic component such as a capacitor may be mounted on the substrate 20.

Further, if the identification resin R2 is visible, the area of the identification resin R2 may be less than 0.03 mm². For example, the area of the identification resin R2 may be in the range of 0.1 mm² or more and 0.5 mm² or less. Further, the area of the identification resin R2 may be larger than 1.7 mm² as long as the identification resin R2 does not wrap around downward.

While embodiments of the invention have been described and illustrated above, it should be understood that these are slope of the invention and are not to be considered as limiting. Additions, omissions, substitutions, and other modifications can be made without departing from the scope of the invention. Accordingly, the invention is not to be considered as being limited by the described description and is only limited by the scope of the appended claims.

What is claimed is:

1. An imaging module comprising:
    an imaging element comprising:
        a light receiving surface;
        an electrode surface on a side opposite to the light receiving surface; and
        imaging element electrodes disposed on the electrode surface;
    a substrate comprising:
        a first surface;
        a second surface on a side opposite to the first surface; and
        a first end surface facing the electrode surface;
    a cable portion comprising a conductor electrically connected to the imaging element electrodes via a wire on the substrate;
    a sealing resin that covers at least the first surface and the second surface; and
    an identification resin attached to a portion of the sealing resin on the first surface or a portion of the sealing resin on the second surface, wherein
    a boundary between the sealing resin and the identification resin has a circular shape or an elliptical shape when viewed from a thickness direction of the substrate; and wherein among the sealing resin and the identification resin, one of the sealing resin and the identification resin is white and the other is black.

2. The imaging module according to claim 1, wherein the identification resin is an ultraviolet curable resin.

3. The imaging module according to claim 2, wherein the identification resin that is a cured ultraviolet curable resin is disposed on a surface of the sealing resin.

4. The imaging module according to claim 1, wherein, when viewed from the thickness direction of the substrate, an area of the identification resin is 1.7 mm² or less.

5. The imaging module according to claim 1, wherein the cable portion comprises a coaxial cable.

6. The imaging module according to claim 1, wherein, when viewed from the thickness direction of the substrate, an area of the identification resin is 0.03 mm² or more.

7. The imaging module according to claim 1, wherein the sealing resin is an ultraviolet curable resin or a thermosetting resin.

8. The imaging module according to claim 1, wherein the identification resin is visually distinguishable from the sealing resin.

* * * * *